United States Patent [19]
Bourgeois et al.

[11] Patent Number: 6,091,992
[45] Date of Patent: *Jul. 18, 2000

[54] METHOD AND APPARATUS FOR ELECTRICAL STIMULATION OF THE GASTROINTESTINAL TRACT

[75] Inventors: Ivan Bourgeois, Verviers, Belgium; Johan Ryden, Beek, Netherlands

[73] Assignee: Medtronic, Inc., Minneapolis, Minn.

[*] Notice: This patent is subject to a terminal disclaimer.

[21] Appl. No.: 08/990,984

[22] Filed: Dec. 15, 1997

[51] Int. Cl.$^7$ ...................................................... A61N 1/36
[52] U.S. Cl. .............................................. 607/40; 607/72
[58] Field of Search ................................ 607/40, 41, 73, 607/133, 138, 143; 600/29, 30

[56] References Cited

U.S. PATENT DOCUMENTS

| | | |
|---|---|---|
| 4,981,470 | 1/1991 | Bombeck, IV . |
| 5,188,104 | 2/1993 | Wernicke et al. . |
| 5,292,344 | 3/1994 | Douglas . |

FOREIGN PATENT DOCUMENTS

| | | |
|---|---|---|
| 2 237 648 | 7/1973 | France . |
| 2 453 630 | 4/1979 | France . |
| 0571 938A2 | 5/1993 | Germany . |
| 1651918A1 | of 0000 | U.S.S.R. . |
| WO 94/27672 | 5/1994 | United Kingdom . |

OTHER PUBLICATIONS

Ergebnisse der Inneren Medizin und Kinderheilkunde—16:198 (1961) (cover page).
Electric Stimulation of the Gastrointestinal Tract—GP Apr. 1994.
Gastrointestinal Pacing—A New Concept in the Treatment of Ileus—Biomedical Sciences Instrumentation vol. 1. 1963 (A.M. Bilgutay, R. Wingrove, W.O. Griffen, R.C. Bonnabeau and C.W. Lillehei).
Gastro–intestinal Pacing: Will It Work?—American Journal of Surgery, Feb. 1966 (J. Sonneland).
Evaluation of the Intrinsic Innervation of the Internal Anal Sphincter using Electrical Stimulation—Gut, 1989, 30, 935–938 (M.A. Kamm, J.E. Lennard–Jones, and R.J. Nicholls).
Enhancing Absorption in the Canine Short Bowel Syndrome by Intestinal Pacing—Surgery, Aug. 1980 (H.E. Gladen and K.A. Kelly).
Pacing the Human Stomach—Surgery, Feb. 1992 (B.W. Miedema, M.G. Sarr and K.A. Kelly).
Ectopic Jejunal Pacemakers and Gastric Emptying after Roux Gastrectomy: Effect of Intestinal Pacing—Surgery, Nov. 1989 (L.Karlstrom and K.A. Kelly).
A New Treatment for Rectal Prolapse (Abridged)—Proceedings of the Royal Society of Medicine (K.P.S. Caldwell).
Prognosis of Patients with an Ileostomy—Section of Proctology (A.G. Parks).
Differential Responses of the Canine Gastric Corpus and Antrum to Electric Stimulation—American Journal of Physiology, Jan. 1974 (K.A. Kelly).
The Electrical Control of Sphincter Incompetence—The Lancet, Jul. 23, 1963 (K.P.S. Caldwell).
Gastric Motor Physiology and Pathophysiology—Surgical Clinics of North America, vol. 73, Dec. 1993 (J.J. Cullen and K.A. Kelly).
The Role of the Extrinsic Antral Nerves in the Regulation of Gastric Emptying—Surgery, Gynecology & Obstetrics, Sep. 1977, vol. 145 (C.T. Mroz and K.A. Kelly).

(List continued on next page.)

Primary Examiner—Jeffrey R. Jastrzab
Attorney, Agent, or Firm—Thomas F. Woods; Michael J. Jaro; Harold Patton

[57] ABSTRACT

A method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach.

32 Claims, 12 Drawing Sheets

OTHER PUBLICATIONS

A New Treatment for Rectal Prolapse—Geriatrics, Jan. 1968 (K.P.S. Caldwell).

Incontinence—Transactions of The Medical Society of London, Ordinary Meeting, Apr., 1973 (K.P.S. Caldwell).

The Treatment of Incontinence—Hospital Management (K.P.S. Caldwell).

Control of Gastro–intestinal Motility with Electrical Pacing—Jap. J. Smooth Muscle Res. 21: Suppl., 125, 1985 (H.M. Richter, III, S. Bjorck and K.A. Kelly).

Effect of Electrical Stimulation on Gastric Electricla Activity, Motility and Emptying—Neurogastroenterology and Motility 1995 (J.C. Eagon and K.A. Kelly).

Independence of Canine Gastric and Duodenal Pacesetter Potentials Shown by Electric Pacing—May Clin. Proc, Jan. 1977, vol. 52 (H.E. Gladen and K.A. Kelly).

Duodenal–Gastric Refulx and Slowed Gastric Emptying by Electrical Pacing of the Canine Duodenal Pacesetter Potential—Gastroenterology 72:429–433, Mar. 1977 (K.A. Kelly and C.F. Code).

Pacing the Human Gut—The American Journal of Gastroenterology, vol. 89, No. 3, 1994 (D.A. Johnson and E.L. Cattau).

Pacing the Gut—Gastroenterology, Dec. 1992 (K.A. Kelly).

Human Gastric Myoelectric Activity and Gastric Emptying Following Gastric Surgery and With Pacing—1992 Gastroenterological (M.P. Hocking, S.B. Vogel and C.A. Sninsky).

Pacing the Canine Stomach with Electric Stimulation—American Journal of Physiology, Mar. 1972 (K.A. Kelly and R.C. La Force).

Gastric Emptying of Liquids and Solids: Roles of Proximal and Distal Stomach—Editorial Review, The American Physiological Society 1980 (K.A. Kelly).

Electric Pacing of Intact and Transected Canine Small Intestine and its Computer Model—American Journal of Physiology, vol. 229, Nov. 1975 (O.E. Akwari, K.A. Kelly, J.H. Steinbach and C.F. Code).

Electrical Treatment for Anal Incontinence—The Lancet, Feb. 5, 1966 (B.R. Hopkinson, R. Lightwood).

Electrophysiology of Human Colon Motility in Health and Disease—Clinics in Gastroenterology, vol. 15, No. 4, Oct. 1986 (J.D. Huizinga).

Cerebral Evoked Potentials After Rectal Stimulation—Electroencephalography and Clinical Neurophysiology, 80 (1991) 490–495 (V. Loening–Baucke, N.W. Read and T. Yamada).

Measurement of Gastric and Small Bowel Electrical Activity at Laparoscopy—Journal of Laparoendoscopic Surgery, vol.4, No. 5, 1994 (B.O. Familoni, T.L. Abell and G. Voeller).

Electrical Stimulation of the Bowel—Arch Surg. vol. 91, Sep. 1965 (J.M. Moran and D.C. Nabseth).

Electrical Pacing for Short Bowel Syndrome—Surgery, Gynecology & Obstetrics—Nov. 1981, vol. 153 (H.E. Gladen and K.A. Kelly).

The Treatment of Incontinence by Electronic Implants—Annals of The Royal College of Surgeons of England, Dec. 1967 (K.P.S. Caldwell).

The Future of Intestinal Pacing—Gastroenterology Clinics of North America, vol. 23, No. 2, Jun. 1994 (J.J. Cullen and K.A. Kelly).

Control of Muscle Tone in the Human Colon—Gut, 1992, 33, 541–546 (C.J. Steadman, S.F. Phillips, M. Camilleri, N.J. Talley, A. Haddad, R. Hanson).

Enhancing the Anti–Dumping Effect of Roux Gastrojejunostomy with Intestinal Pacing—Ann. Surgery, Oct. 1983, vol. 198 (B. Cranley, K.A. Kelly, V.L.W. Go, L.A. McNichols).

The Roux Operation for Postgastrectomy Syndromes—The American Journal of Surgery, vol. 161, Feb. 1991 (B.W. Miedema, K.A. Kelly).

Effect of Duodenal Cooling on Small Intestinal Pacing—Mayo Clin. Proc. Aug. 1982, vol. 57 (K.R. Berg, H.E. Gladen, K.A. Kelly).

Achieving Enteric Continence: Principles and Applications—Mayo Clin Proc. Jul. 1986, vol. 61 (J.H. Pemberton, K.A. Kelly).

Electrical Stimulation of the Human Stomach—Digestive Diseases and Sciences, vol. 30, No. 8, Aug. 1985 (W.E. Waterfall, D. Miller, D.N. Ghista).

Gastric Electrical Stimulation as a Possible New Therapy for Patients with Severe Gastric Stasis—Gastroenterology, vol. 100, No. 5, Part 2 (T.L. Courtney, B.D. Schirmer, B.E. Ballahsene, O.L. Updike and R.W. McCallum).

Temporary and Permanent Electrical Stimulation of the Human Stomach Using High Frequency Pacing—Motility and Nerve–Gut Interactions, Apr. 1993 (B.O. Familoni, T.L. Abell, G. Voeller, A. Salem, O. Gaber, D. Nemoto).

Long–Term Electrical Stimulation of the Human Stomach—Gastroenterology, vol.106, No. 4, Part 2 (B.O. Familoni, T.L. Abell, G. Voeller, A. Salem, O. Gaber, D. Nemoto).

A Model of Gastric Electrical Activity in Health and Disease—IEEE Transactions on Biomedical Engineering, vol. 42, No. 7, Jul. 1995 (B.O. Familoni, T.L., Abell, K.L. Bowes).

Use of Spectral Analysis in the Detection of Frequency Differences in the Electrogastrograms of Normal and Diabetic Subjects—IEEE Transactions on Biomedical Engineering, vol. 35, No. 11, Nov. 1988 (C.J. Pfister, J.W. Hamilton, N. Nagel, P. Bass, J.G. Webster and W.J. Tompkins).

Gastric Motility after Gastric Operations—Surgery Annual 1974 (K.A. Kelly).

Electrical Stimulation of Gastric Electrical Control Activity—American Journal of Physiology, vol. 225, No. 1, Jul. 1973 (S.K. Sarna and E.E. Daniel).

Electrical Pacing of the Roux Limb Resolves Delayed Gastric Emptying—Journal of Surgical Research 42, 635–641 (1987) (A. Sawchuk, D. Canal, J.L. Grosfeld, <. Slaughter, G. Gardner, T. O'Connor and D. Behrman).

Gastrointestinal Pacing—Staff Report Meeting—University of Minnesota Medical Bulletin 1965 (A.M. Bilgutay, R. Wingrove, W.O. Griffen, A. Nakib, R.C. Bonnabeau, C.W. Lillehei).

Acceleration of Gastric Emptying with Electrical Stimulation in a Canine Model of Gastroparesis—1992 the American Physiology Society (B–E Bellahsène, C.D. Lind, B.S. Schirmer, O.L. Updike and R.W. McCallum).

A Trial of a Gastro–intestinal Pacemaker—Journal of the Irish Medical Association Jan. 1966 (P.N. Fitzpatrick, and A.W. Chen).

Behavioral and Gastrointestinal Changes (Motility and Blood Flow) Induced by Electrical Stimulation of the Lateral Hypothalamus in Cats—Abstr. XI Scand. Physiol. Congr. Copenmhagen 1963, Suppl. No. 213 (F. Björn and E.H. Rubinstein).

Gastrointestinal Pacemaker—The Lancet, Dec. 7, 1963 (J.M. Sanchez).

Gastrointestinal Pacing—Modern Medicine, Mar. 15, 1965 (A.M. Bilgutay, R. Wingrove, W.O. Griffen, A. Nakib, R.C. Bonnabeau and C. W. Lillehei).

Response to Gastrointestinal Pacing: Antral, Duodenal and Jejunal Motility in Control and Postoperative Patients—Annals of Surgery, Jul. 1966 (T. Berger, J. Kewenter, N.G. Kock).

Evaluation of a Portable Gastric Stimulator—IEEE/9th Annual Conference of the Engineering in Medicine and Biology Society, 1987 (B–E. Bellahsene, R.W. McCallum, O.T. Updike).

Role of Gastric Pacesetter Potential Defined by Electrical Pacing—Canadian Journal of Physiology and Pharmacology, vol. 50, Oct. 1972 (K.A. Kelly and R.C. La Force).

The Endomotorsonde—A New Device for Studying the Gastrointestinal Tract—The American Journal of Medical Electronics, Jul.–Sep. 1964 (J.P.M. D'Haens).

Electronic Pacemakers of the Heart, Gastrointestinal Tract, Phrenic Nerve, Bladder and Carotid Sinus: Current Status—Surgery, Aug. 1966, vol. 60, No. 2 (C.E. Anagnostopoulos, W.W.L. Glenn).

Control of Postoperative Adynamic Bowel in Dogs by Electric Stimulation—vol. IX Trans. Amer. Soc. Artif. Int. Organs, 1963 (D. R. de Villiers, I. Saltiel, A. Nonoyama and Y. Kantrowitz).

Reverse Electrical Pacing Improves Intestinal Absorption and Transit Time—Surgery, vol. 100, No.2, Aug. 1986 (A. Sawchuk, W. Nogami, S. Goto, J. Yount, J.A. Grosfeld, J. Lohmuller, M.D. Grosfeld and J.L. Grosfeld).

External Stimulation of Gastric Antrum and Gastric Secretion—The American Journal of Gastroenterology, vol. 52, No. 6, Dec. 1969 (P. Lott, T. Geisel, N.C. Jefferson and H. Necheles).

Electrical Activity of the Gastric Antrum in Normal Human Subjects—The American Journal of Digestive Diseases, vol. 16, No. 7, Jul. 1971 (H. Monges and J. Salducci).

Gastric Pacemakers—Gastroenterology, vol. 70, No. 2, Feb. 1976 (S.K. Sarna, K.L. Bowes and E.E. Daniel).

Apparatus for Electrical Stimulation of Weakened Peristaltic Activity of the Stomach (Experimental Investigation)—Biomedical Eng. Mar.–Apr. 1973 (M.A. Sobakin and V.A. Shepelev).

Clinical Evaluation of the Gastrointestinal Pacer—Surgery, Gynecology & Obstetrics, Jan. 1965 (D.C. Quast, A.C. Beall and M.E. DeBakey).

Electrostimulation of the Small and the Large Bowel in Dogs—Biomedical Sciences Instrumentation, May, 1969 (G. Járos and C.R. Jansen).

Clinical Experience in Control of Postoperative Adynamic Ileus by Electric Stimulation—Surgical Forum, Vo.. 14, 1963 (D.R. de Villiers, I. Saltiel, A. Nonoyama and A. Kantrowitz).

Electric Treatment of Intestinal Obstruction and Postoperative Paralysis of the Bowel—Journ. A.M.A., Apr. 1, 1911 (W.H. Dieffenbach).

Studies in Electrical Stimulation of the Adynamic Bowel—The American Journal of Gastroenterology, vol. 44, 1965 (A. Kantrowitz).

Electrical Activity of the Gastrointestinal Tract as an Indication of Mechanical Activity—American Journal of Digestive Diseases, vol. 8, 1963 (E.E. Daniel and K.M. Chapman).

Relative Electrical Impedance as Index of Intestinal Viability—Archives of Surgery, vol. 89, Jul. 1964 (L.C. Carey, K. Kayser, E.H. Ellison and D. Lepley).

Controlled Radiological Evaluation of an Intestinal Pacemaker (Peristart)—Scand. J. Gastroent., 1966, vol. 1 (P. Bach–Nielsen, H. Baden and A.M. Christensen).

An Improved Method for Recording and Analyzing the Electrical Activity of the Human Stomach—IEEE Transactions on Biomedical Engineering, vol. 32, No. 11, Nov. 1985 (B.E. Bellahsene, J.W. Hamilton, J.G. Webster, P. Bass and M. Reichelderfer).

Study of Transcutaneous and Intraluminal Measurement of Gastric Electrical Activity in Humans—Medical & Biological Engineering & Computing, Jul. 1987 (B.O. Familoni, Y.J. Kingma and K.L. Bowes).

Human Gastric Myoelectric Activity and Gastric Emptying Following Gastric Surgery and With Pacing—Gastroenterology, 1992, vol. 103, No. 6 (M.P. Hocking, S.B. Vogel and C.A. Sninsky).

Programmer Medtronic 7432 and Memory Mod 7455—Clinical Plan Gastroparesis, Mar. 2, 1994.

Electrical Pacing of the Stomach in Dogs—IEEE, Sep. 1992 (B.O. Familoni, T.L. Abell).

Gastroparesis and the Current Use of Prokinetic Drugs—The Gastroenterologist, vol. 1 No. 2, Jun. 1993 (B.J. Kendall and R.W. McCallum).

Physiology of the Colon and Rectum—The American Journal of Surgery, vol. 117, Jun. 1969 (R.D. Williams and J.W. Dickey).

Effects of Gastric Pacing on Canine Gastric Motility and Emptying—American Journal of Physiology, vol. 265, No. 4, Oct. 1993 (J.C. Eagon and K.A. Kelly).

Manometric Evaluation of Children with Chronic Constipation Using a Suction Stimulating Electrode—Eur. J. Pediatr. Surg. 2 (1992)287–290 (M. Kubota, A. Nagasaki and K. Sumitomo).

"High Prevalence of Gastric Electrical Dysrhythmias InDiabetic Gastroparesis"—T.L. Abell et al. (Gastroenterology, 1985; 88:1299).

"Development of a Canine Model for Gastric Pacing"—B. Johnson et al. (Gastroenterology, vol. 98, No. 5, Part 2).

"Postoperative Gastroparesis and Tachygastria—Response to Electric Stimulation and Erythromycin"—M.P. Hocking (Surgery, vol. 114, No.3, Sep. 1993, pp. 538–542).

"Electrogastrographic Study of Gastric Myoelectrical Activity in Patients with Unexplained Nausea and Vomiting"—H. Geldof et al. (Gut, 1986, vol. 27, pp. 799–808).

"Efficacy of Electrical Stimulation at Frequencies Higher than Basal Rate in Canine Stomach"—B. Familoni et al. (Digestive Diseases and Sciences, vol. 42, No. 5, May 1997, pp. 892–897.

"Analysis of Gastric Emptying Data"—J.D. Elashoff et al. (Gastroenterology 1982:83; pp. 1306–1312).

"Gastric Myoelectric Activity in Patients with Chronic Idiopathic Gastroparesis"—M. Bortolotti et al. (Gastrointestinal Motility, vol. 2, No. 2, Jun. 1990, pp. 104–108).

GastricElectromechanical and Neurohormonal Function in Anorexia Nervosa:—T.L. Abell et al. (Gastroenterology, Nov. 1987:93: pp. 958–965).

Electrogastrography—Current Assessment and Future Perspectives—T.L. Abell et al. (Digestive Diseases and Sciences, vol. 33, No. 8, Aug. 1988, pp. 982–992).

Electrogastrographic Study of Patients with Unexplained Nausea, Bloating and Vomiting—C.H. You et al. (Gastroenterology, vol. 79, No. 2, Aug. 1980, pp. 311 314).

"Motility of the Stomach and Gastroduodenal Junction"—K.A. Kelly (Physiology of the Gastrointestinal Tract, 1981, pp. 393–410).

"Gastric Dysrhythmias and Nausea of Pregnancy"—K.L. Koch et al. (Digestive Diseases and Science, vol. 35, No. 8, Aug. 1990, pp. 961–968).

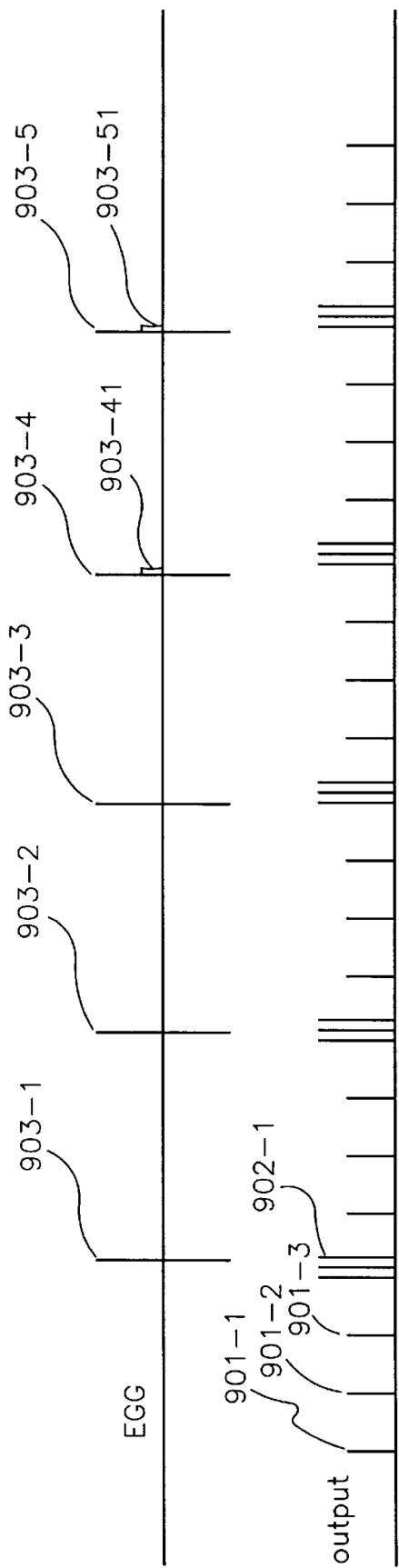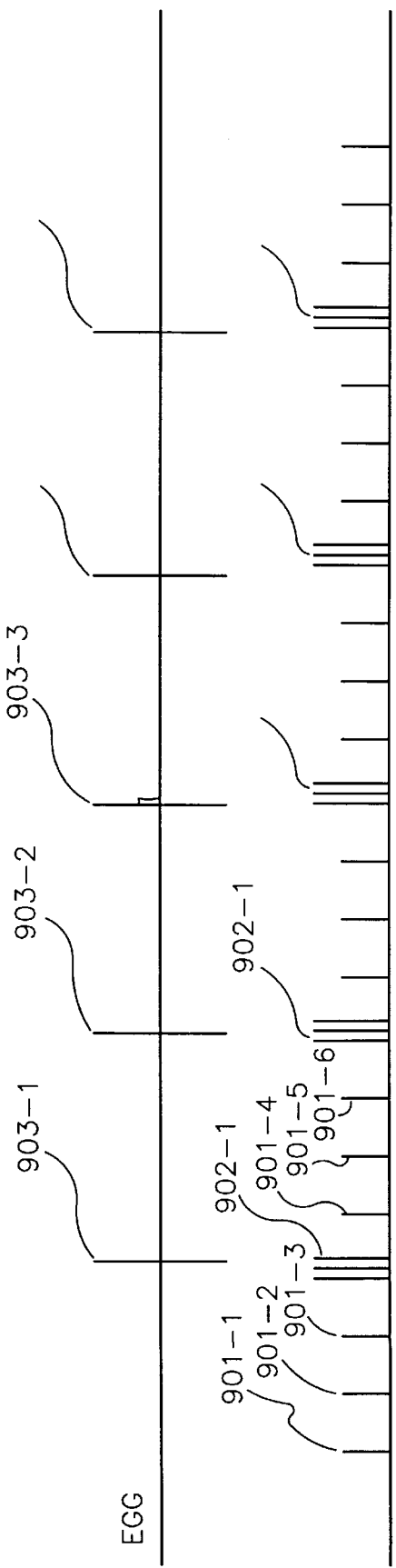

METHOD AND APPARATUS FOR ELECTRICAL STIMULATION OF THE GASTROINTESTINAL TRACT

FIELD OF THE INVENTION

The invention relates to treatment of gastrointestinal disorders using a method and apparatus for providing electrical stimulation of the gastrointestinal tract.

BACKGROUND OF THE INVENTION

The gastrointestinal tract is responsible for an essential step in the digestive process, the reception of nutrition in the human body. An important element of the digestive process is peristalsis, the coordinated and self-regulated motor activity of the intestinal tract. Peristalsis is accomplished through a coordinated combination of electrical, chemical, neurological and hormonal mediation, as well as possibly other, as yet unknown, mechanisms.

Many diseases and maladies can affect the motor activity of the gastrointestinal tract, causing malfunction of the digestive process. Such diseases include diabetes mellitus, scleroderma, intestinal pseudo-obstruction, ileus, and gastroparesis.

Gastroparesis, for example, is a chronic gastric motility disorder in which there is delayed gastric emptying of solids and/or liquids. Symptoms of gastroparesis may range from early satiety and nausea in mild cases to chronic vomiting, dehydration, and nutritional compromise in severe cases. Diagnosis of gastroparesis is based on demonstration of delayed gastric emptying of a radio-labeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the gastrointestinal tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

Presently, however, there is no practically effective device or system to stimulator intelligently alter the muscular contractions of smooth muscle and the gastrointestinal tract in particular. Therefore, there is a need in the art for a system and method to properly stimulate the gastrointestinal tract to thereby treat ineffective or absent electrical muscular activity of the gastrointestinal tract.

Patients suffering from gastroparesis have two symptoms which should be treated. First, many patients suffer from vomiting, nausea, bloating and abdominal pain. Second, many patients further suffer from motility disorders, i.e. the peristaltic contractions of the gastrointestinal organ is either inhibited or completely absent.

SUMMARY OF THE INVENTION

It is an object of the invention to provide a method and apparatus for treating patients having dysfunctional gastrointestinal muscle or disorders of smooth muscles elsewhere in the body.

This and other objects are provided by one or more of the embodiments described below. The present invention is a method and apparatus for providing electrical stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably provides stimulation to the gastrointestinal organ with a first type of pulse train at a first rate to treat vomiting and with a second pulse train at a second rate to increase motility. In the preferred embodiment, as discussed below, the first type of pulse train is delivered at approximately 12 bpm while the second type of pulse train is delivered at a much slower rate, typically around 3 bpm. Through this stimulation, using two unique types of pulse trains at two distinct rates of delivery, both the symptoms of vomiting and lack of motility may be treated.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein:

FIG. 6 depicts the operation of the present invention while in an asynchronous mode, i.e. the stimulating pulse trains are provided regardless of the intrinsic activity of the gastrointestinal organ.

FIG. 7 depicts an alternate mode in which the device may operate.

The FIGS. are not necessarily to scale.

DETAILED DESCRIPTION OF THE INVENTION

Figure 1:
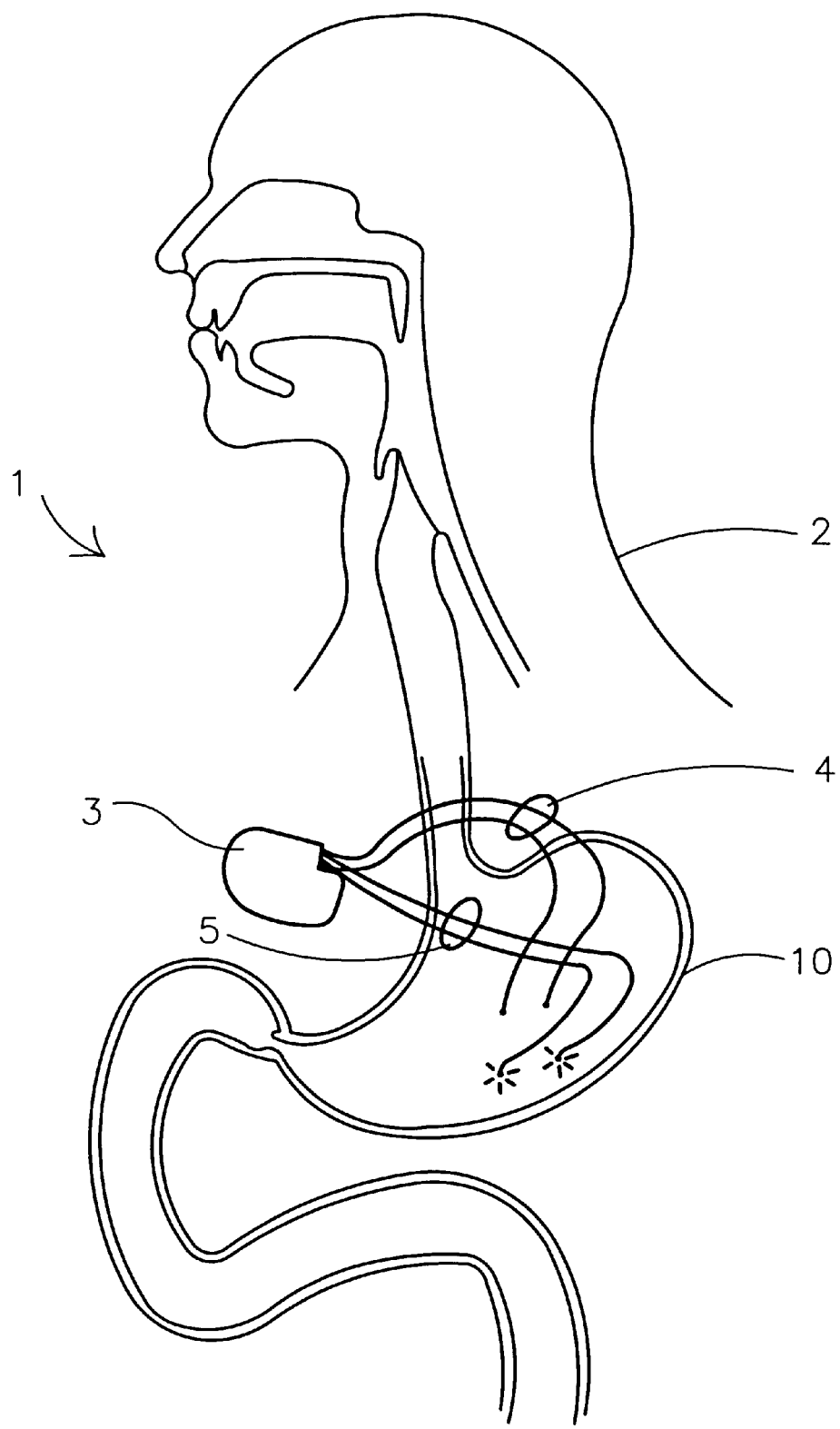
FIG. 1 depicts the apparatus implanted within a patient.

FIG. 1 shows a system 1 implanted in a patient 2. As seen, the system 1 comprises an implantable pulse generator 3 featuring two sets of leads 4, 5 which are coupled to the stomach 10. The first set of leads 4 provide stimulation to the stomach. The second set of leads 5 provide sensing of the gastroelectrical activity of the stomach 10 to the pulse generator 3. In the preferred embodiment, the pulse generator 3 is implanted within the patient 2. As such, the implantable pulse generator 3 features a hermetic enclosure, as is well known in the art. The leads used for both the first set 4 and the second set 5 may be any acceptable lead. In the preferred embodiment, the preferred leads are Medtronic Model No. 4300 intramuscular lead. Of course, other configurations of leads or lead systems may be used, including the use of from only a single lead, a single set of leads (i.e. two), or even the use of three or more sets of leads. Moreover, although shown as being coupled to the stomach it must be understood the present invention may be used along or on any of the other structures and organs along the gastrointestinal tract, including the colon, small intestine, stomach or even the esophagus.

The first set of leads 4 are stimulation leads which conduct stimulation pulses from the pulse generator 3 to the stomach 10. First set of leads 4 are preferably implanted through the serosa at the area within the transition of the corpus and the antrum on the great curvature. Of course, other locations for first set of leads 4 may be used, such as in the fundus, caudud corpus as well as the orad or terminal antrum. The second set of leads 5 are sensing leads which conduct any gastroelectrical activities sensed in the stomach 10 to the pulse generator 3. Preferably the second set of leads 5 are positioned distally in the mid antrum also along the great curvature, although these leads may also be positioned in other locations.

Figure 2:
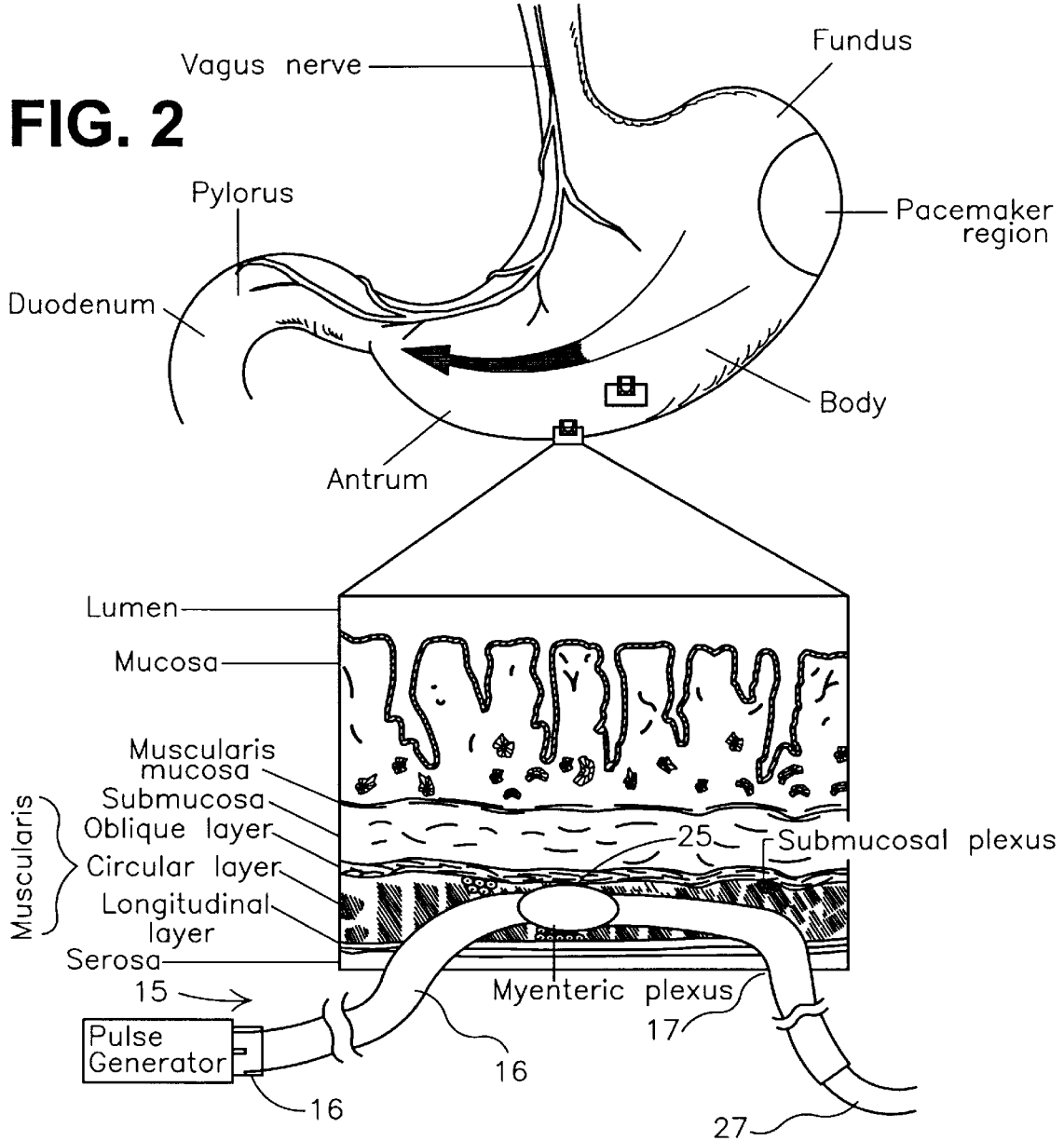
FIG. 2 depicts a detailed view of the stomach muscle showing the electrode of the lead implanted.

FIG. 2 details the preferred positioning of an electrode of a lead within the various layers of the stomach. As seen, the stomach 10 has essentially seven layers of tissue. In the preferred embodiment, the electrode of each lead is positioned into the layers of the stomach muscle as shown. That is, the electrode is positioned such that it intersects both the longitudinal and circular layers. This is believed important by the inventor because in such a manner the electrode is able to also intersect the enteric nervous system of the stomach and be in close contact with the cells of Cajal. This is believed important as research has shown that intramuscular electrodes may effectively stimulate the stomach with less than one one-thousandths of the energy required for serosal electrodes. Of course, other types of electrodes or lead systems may be used, including those which contact only any one of each of the layers of the stomach organ, such as only the mucosa or only the serosa. Moreover, although in the preferred embodiment a pair of unipolar leads are used for stimulation and a second pair of unipolar leads are used for stimulation, other configurations of leads may be used, such as bipolar, tripolar, quadrapolar, as well as any other configuration suitable such as a unipolar lead and can.

Figure 3:
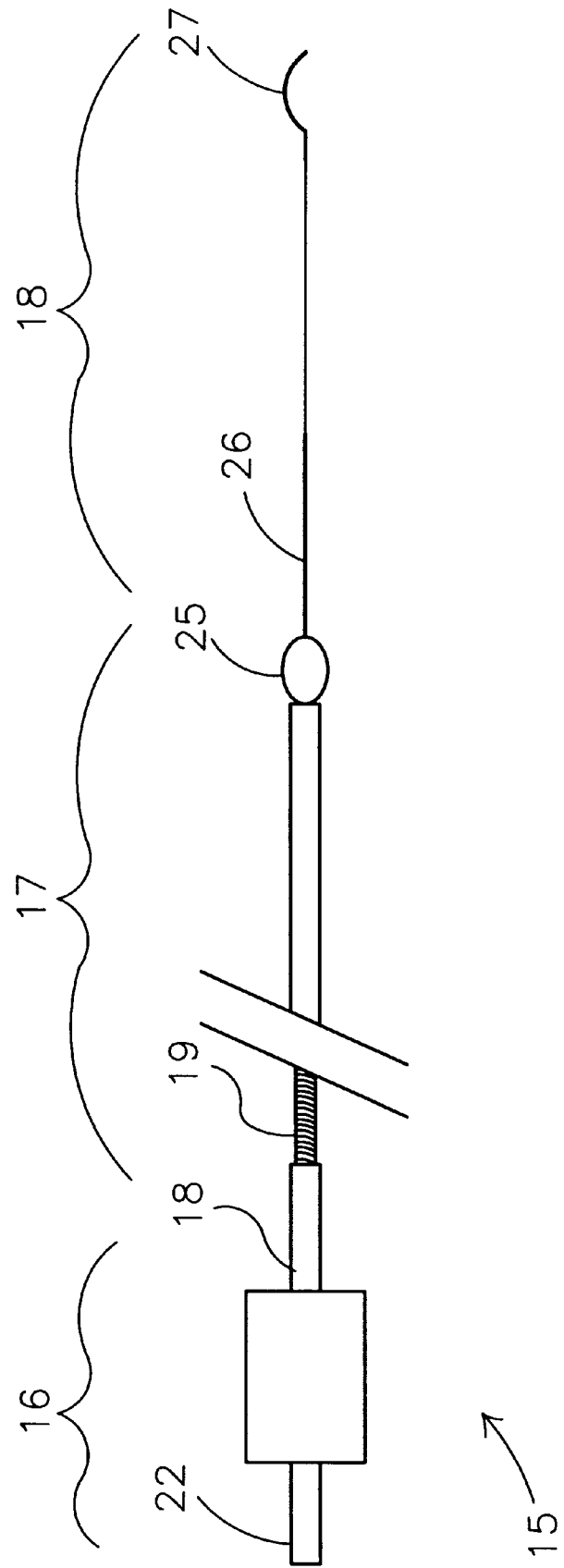
FIG. 3 depicts a plan view of a lead used with the apparatus.

FIG. 3 depicts a plan view of the preferred embodiment lead 15 used in the present invention. As seen, the lead 15 essentially has three sections, connector section 16, body section 17 and fixation section 18. Connector section 16 includes a connector pin 22 to electrically couple the lead 15 into the pulse generator. Any connector pin 22 as well known in the art may be used. Body section 17 includes an electrical conductor 19 surrounded by an electrical insulator 20. In the preferred embodiment electrical conductor 19 is a platinum iridium alloy and electrical insulator 18 is silicone. Of course, other biocompatible materials may also be used. As seen, at the distal end of the body section 17 is an electrode 25. In the preferred embodiment, electrode 25 is a polished platinum iridium alloy. Of course, other materials may likewise be used, such as a porous platinized structure. In addition, the electrode 25 could further feature various pharmaceutical agents, such as dexamethasone sodium phosphate or beclomethasone phosphate in order to minimize the inflammatory response of the tissue to the implanted lead 15. Other agents such as antibiotics may also be used. Located distal to the electrode 25 is the fixation section 18. As seen, fixation section 18 has essentially two piece parts, a suture 26 which is in turn coupled to a needle 27. Needle 27 is preferably curved. In an alternate embodiment suture may feature a fixation coil as is well known in the art to cooperate with the body tissue after implantation to maintain the lead 15 in the position implanted. Of course, other fixation mechanisms may be used, such as fixation discs, as is well known in the art.

Figure 4:
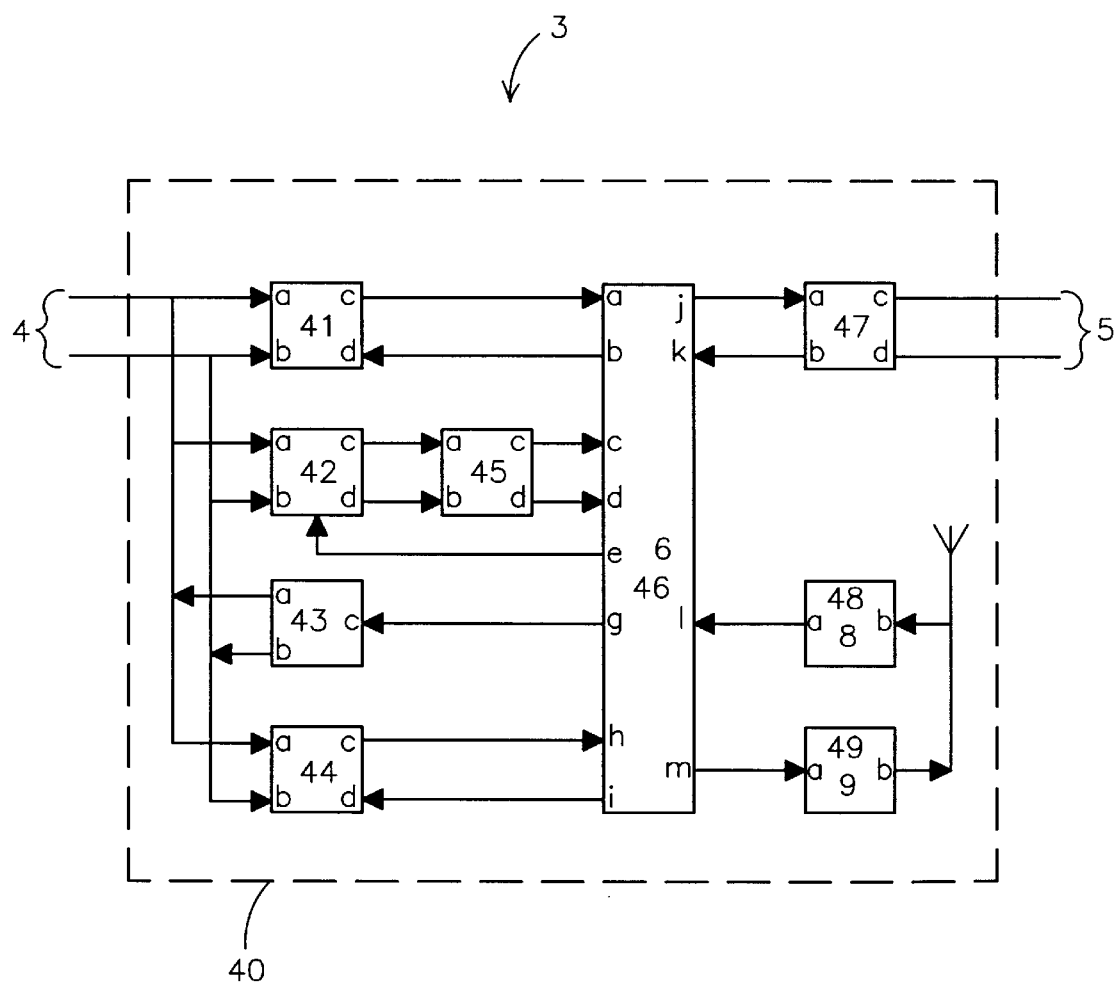
FIG. 4 is a functional block diagram of the pulse generator.

FIG. 4 depicts a functional block diagram of the gastrointestinal pulse generator according to the present invention. As seen, pulse generator 3 is enclosed by hermetic enclosure 40 to the electronics and battery while the device is implanted. Hermetic enclosure may consist of any suitable construction. Pulse generator 3 couples with two sets of leads 4, 5 which are, in turn, coupled to the stomach 10. The first set of leads 4 transmits stimulation pulses from pulse generator 3 to the stomach. The second set of leads 5 provide sensing of the gastroelectrical activity of the stomach 10 to the pulse generator 3. Although in the preferred embodiment the stimulating leads and sensing leads are separate leads, the present invention may also be employed using a combination of lead which both sense and stimulate.

As seen, the sensing leads 4 are coupled into a slow wave detection circuit 41. Slow wave detection circuit 41 includes a band pass amplifier, a slew rate converter and two threshold detectors. Essentially, such a slow wave detection circuit 41 is similar to those used in a cardiac pacemaker but with several important characteristics. First, the band pass amplifier has a much lower center frequency, preferably on the order of 0.3 HZ but anywhere between approximately 0.1 and 0.5 Hz may be used in the stomach. Of course, the present invention may be used in each of the various organs along the gastrointestinal tract so that the center frequency may be varied accordingly. The slew rate converter operates in a manner well known in the art and generates a signal corresponding to the slew rate of the sensed electrogastrogram. The threshold detectors operates in a manner well known in the art and generate output signals when the sensed input signal is above a threshold level. One threshold detector corresponds to the peak to peak amplitude of the sensed electrogastrogram. The second threshold detector corresponds to the sensed slew rate.

Preferably, the slow wave detection circuit 41 must be able to detect input signals between approximately 30 microvolts and 10 millivolts which have a slew rate between approximately 100 microvolts per/second up to 10 volts per/second with a typical value of 100 millivolts per second. Such a range may be achieved using multiple steps which are controlled by the microprocessor 46 via the input line 46b–41d. To detect the slow wave, both threshold detectors should be coupled using a logical AND configuration. Thus, a signal should then be sent via the output line 41c–46a to the microprocessor 46. The slew rate detector may also include an interference detector specially designed to detect continuous interference, especially at any of the various mains frequencies of power distribution (e.g. 16–400 Hz) so that false sensing is avoided. In an alternative embodiment a second sense amplifier may be provided having a bandpass in the range of expected power field variations in various frequencies of power distribution (e.g. 16–400 Hz). At every cycle the presence of interference is detected. The time interval between approximately two detections is measured and if this time interval corresponds to any of the main frequencies of power distribution which is preprogrammed, then this detection is labeled as interference and the detection on the other amplifier will be simultaneously labeled also as interference detection and not as a valid slow wave sensors for sensing intrinsic gastrointestinal electrical activity may also sense signals having frequencies ranging approximately between 100 Hz and 300 Hz.

The band pass amplifier in the detection circuit 41 should be blanked for a period after a sensed event has been received by the microprocessor 46 or just before and during a stimulation pulse is emitted by output stage discussed below. Blanking may be accomplished through either a blanking switch which disconnects the amplifier from the electrodes or through a program performed in the microprocessor. The microprocessor 46 should also ignore sensed output signals during a period after a sensed or paced event. This is similar to a blanking circuit where sensed events during a blanking period do not affect the timing of the pulse generator. In the preferred embodiment, the blanking period for slow wave detection is on the order of between approximately 0.5 to 4.0 seconds.

Generally speaking, the blanking period decreases with increasing slow wave frequency. The blanking period algorithm is controlled by the microprocessor. The blanking period algorithm operates such that when the slow wave interval is shortened the blanking period is also shortened. This shortening may be performed in any manner, for example, in a linear fashion or in some other more complex monotonous fashion. After the blanking period, during a certain timing window, the microprocessor 46 is able to receive slow wave detection signals, which will not restart the pulse generator timing circuit, but will instead be interpreted as interference by the microprocessor 46. This timing window, interference detection timing window, may be up to seven seconds in duration after the sensed or paced event, preferably it is 100 milliseconds. To be precise, the combined blanking period and interference detection windows are shortened. Shortening may occur in any manner desired, i.e. in a linear fashion between approximately a preset high or a preset low value or along a non-linear manner. The shortening of the combined blanking and interference detection interval will not occur once the combined blanking and interference detection window reaches a programmed value, such as 2.5 s. This combined blanking window may also be programmed to be turned off such that it does not change in response to sensed physiologic signals. In all circumstances, however, the interference detection window remains equal to at least 100 ms. For example, the rationale is that the typical main frequencies of power distribution are 50 Hz, 60 Hz, 400 Hz and 16.33 Hz. The lower harmonic for 1633 Hz is 8 Hz which corresponds to an interval of 125 ms. Of course the exact length of time for each period may be programmed by the physician. Moreover, each of the periods may be further made to be automatically adjusted based on the sensed electrical activity.

As seen in FIG. 4, blanking switch 42 couples sensing electrodes 4 to amplifier 45 to detect high frequency spike activity. The operation of blanking switch 42 causes the amplifier 45 to be connected to the sensing electrodes 4 once an intrinsic deflection or slow wave has been detected by slow wave detection circuit 41 or a stimulus has been emitted by output stage 47. Preferably, this occurs after a short delay. Blanking switch 42 is closed between approximately 0.5 to 2 seconds after these events and opens roughly 5 to 7 seconds later or at approximately 30% of the intrinsic event interval. As seen, the switch is controlled via the line 46e–42e.

The detection circuit for the high frequency spike activity detector consists of a bandpass amplifier having the center frequency at approximately 300 Hz. As discussed above, however, the center frequency will vary for different organs. The amplifier is followed by two threshold detectors, the first detector detects peak to peak amplitude while the second detector detects slew rate. Both detectors are coupled using a logical AND configuration. The detector pulses are counted, and the interval between approximately pulses is measured. If the interval corresponds to the intervals of the mains frequencies of power distribution or any of their harmonies, i.e. 20 ms or 10 ms, they are rejected. If the number of pulses exceeds a pre-programmed value, then a contraction is indicated. The counter is provided to store in the memory the time of occurrence of the contraction. The number of pulses corresponding to each contraction may be counted and tallied to determine the strength of the contractions. In the present embodiment 3–5 pulses correspond to a weak contraction; 6–8 pulses correspond to a moderate contraction; 9 or more pulses correspond to a strong contraction. Each of these values, of course, may be programmed and the exact number of pulses will vary due to the implementation.

Also coupled to the sensing electrodes 4 is an AC current generator 43. This AC current generator 43 is part of a plethysmorgraphy circuit. Overall, the plethysmography circuit is present to provide a means for sensing mechanical activity of the underlying tissue. That is, whereas the spike activity in the electrogastrogram may be used to sense contraction, the contraction may also be sensed using the plethysmography circuit. Plethsmography circuit is comprised from AC current generator 43, amplifier, modulator and ADC converter 44 as well as a portion of the microprocessor 46. The AC current generator 43 is switched on via signal from microprocessor 46 once a slow wave is detected or a pacing stimulus is emitted. It is switched off roughly 10 seconds after being switched on also from the same line or signal from the microprocessor 46. The AC current generator 43 amplitude and frequency are programmable via microprocessor 46. The frequency should be such it is not detected by amplifiers 41, 45, e.g., 1 kHz. If synchronous detection by amplifier 41 occurs at the end of the blanking period, then the amplitude and/or the frequency of the AC current generator 43 is adjusted by the microprocessor 46 to avoid subsequent detection of the generated AC current.

Turning now to the amplifier, the modulator and ADC converter 44, the AC voltage caused by the injection of AC current generator 43 is amplified and demodulated and converted in order to detect impedance changes caused by contractions of the underlying tissue. The ADC converter digitizes the amplitude of the demodulated signal. The digitized signal is transmitted via line 44c–46h to the microprocessor 46. The microprocessor 46 analyzes the signal pattern by comparing it with one or more templates to identify it as a contraction as well as to reject interference or signals generated by postural changes or vomiting. This template comparison is done synchronously to the detection of the slow wave. Line 46i–44d is used to control the amplifier and ADC from the microprocessor 46.

The microprocessor 46 handles all timings and data storage of the pulse generator and may be of any suitable design. In the preferred embodiment, a microprocessor 46 such as that used in the Thera I series of Medtronic pacemakers is used. The description of the microprocessor 46 function is described in the section below which details the operation of the algorithm used in the present invention.

Stimulation pulses are generated by the output stage 47. In the preferred embodiment, the output stage 47 generates pulse trains. It should be understood many types of pulse trains or stimulation pulses may be used including constant current or constant voltage outputs, or a mixture of both. The output pulses are transported to the gastrointestinal tissue via medical electrical leads 5 and thus to the stomach.

Turning again to the output stage 47, when an output pulse is to be delivered, its amplitude, pulse width and duration and frequencies are controlled via lines 46j–47a. If it is a burst of stimuli, the frequency and duration are controlled through the same line while a burst finished signal is sent to the microprocessor 46 via output line 47b–46k.

Programmability to the pulse generator 3 is achieved through receiver-demodulator 48 and transmitter 49. As seen, each of these devices is coupled to the microprocessor 46. The receiver-demodulator 48 and transmitter 49 are similar to those used in cardiac pacemakers.

The basic parameter settings such as sensitivity (peak voltage or slew rate), refractory, blanking, output pulse amplitude, pulse width, escape interval and ratio, escape interval to a stimulation interval, are stored in the memory of the microprocessor 46. Default values are also stored. These values can be read from memory and sent to a receiver via the transmitter.

Figure 5:
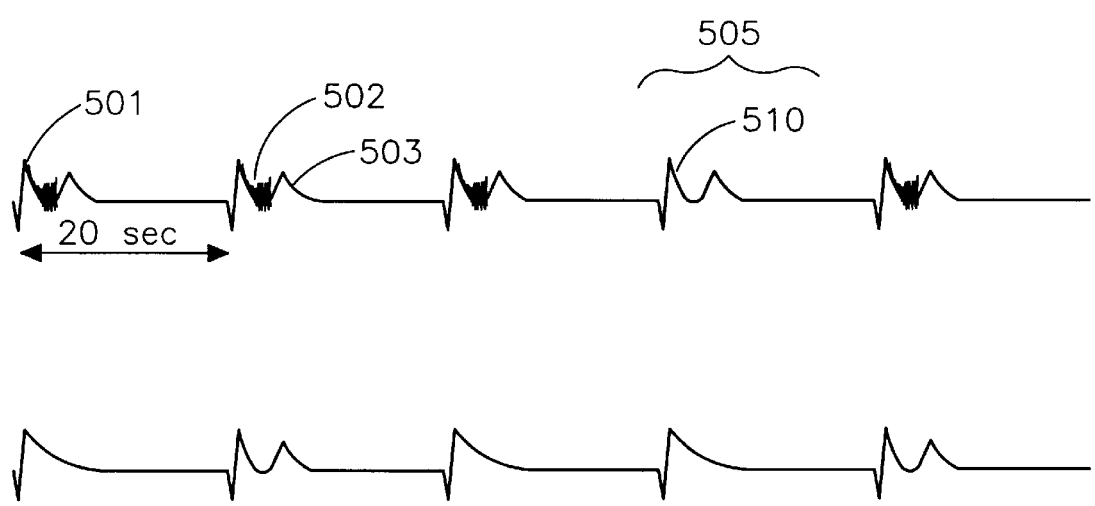
FIG. 5 is an electrogastrogram of the gastrointestinal system.

FIG. 5 shows an electrogastrogram of the stomach in a human. As seen, this intrinsic gastroelectric activity has two distinct components. The first component 501 is a low-frequency, rhythmic depolarization termed slow waves. Superimposed on the slow wave is a high frequency spike activity 502 which corresponds to mechanical contractions of the organ. In the human stomach slow waves are regular, omnipresent depolarizations at 3 cycles/min. (0.05 Hz) that commence high on the greater curvature of the stomach, in the region referred to as the pacemaker region, and propagate aborally, as depicted in FIG. 2.

The normal frequency range for the slow wave in the stomach is between approximately 2.7–3.4 bpm. In clinical situations this value may vary anywhere between approximately 1–15 bpm. High frequency slow wave activity (called tachygastria) does not permit contraction of the stomach readily and may even results in a gastroparesis. In the presence of excessively slow or even absent slow waves (called bradygastria) motility is reduced.

Slow waves and the corresponding spike activity may become irregular or uncoupled or both, thereby preventing the appearance or organization of regular, normally propagated contractions that constitute normal motility. Contractions cannot occur without gastric electrical response activity which is in turn regulated by the electrical control activity. Any disruption in this delicate sequential order may lead to delayed gastric emptying. An example of such an occurrence is shown in complex 505.

The spike activity occurs incidentally for a few of the slow waves while the patient is in a fasting or non-eating condition. This is termed Migratory Motor Complex phase I. Immediately prior to a meal, typically 30 mins, MMC I changes into MMC II. During this phase the number of slow waves having spike activity increases. Once the meal or eating has begun and up to 120 mins after the meal each further slow wave also has a spike activity component. This condition is called MMC III.

As seen in this complex a slow wave 510 occurs which is not followed by any high frequency spike activity. The absence of such activity indicates there is no longer any peristaltic contraction which will occurs, i.e. gastric emptying is delayed.

FIG. 6 depicts the operation of the present invention while in an asynchronous mode, i.e. the stimulating pulse trains are provided regardless of the intrinsic activity of the gastrointestinal organ. As seen, the output channel of the device delivers a first set of low energy pulse trains 901-1 et seq. delivered at a frequency approximately four times the rate of normal slow waves (4 times 3 bpm.) Low energy pulse trains preferably consists of a pulse train delivered at a rate of between approximately 7–27 bpm with 12 bpm preferred and consisting of two pulses, each pulse having an amplitude A, a pulsewidth PW and an inter pulse interval II. II may be anywhere between approximately 6–600 ms in length with 60 ms preferred, A is between approximately 1–50 milliamps with 5 milliamps preferred and pulsewidth is between approximately 3–1000 microseconds with 330 microseconds preferred. Moreover, although the pulse train consisting of two pulses is preferred, any number of pulses between approximately 1–100 may be used. As discussed above, the exact parameters selected depend not only on the organ to be stimulated but also upon the patient's physiology as well as on the preference of the physician attending. As further seen in this FIG. the device also may deliver a high energy pulse train 902. As seen, the high energy pulse train is delivered approximately 3 bpm or 10% above the normal slow wave frequency times per minute. In the preferred embodiment the higher energy pulse train comprises a pulse train of between approximately 1–4 pulses. Each pulse may have an amplitude of between approximately 1 and 7 with 3 Volts preferred and a duration of between approximately 10 to 1000 milliseconds with 330 ms preferred. Each pulse is preferably separated by the delivered pulses in the train by an interval of 100 ms, although this may be anywhere between approximately 120 and 10 ms. In the preferred embodiment the device permits the physician to select any of the above parameters. These parameters are also selected according to the particular organ treated. As seen, this embodiment operates without regard to the underlying activity of the gastrointestinal organ. Thus the various slow waves which occur along the EGG 903-1 et seq. occur and no corresponding activity, simultaneously, is caused to occur along the output channel. As seen, slow waves 903-1, -2 and -3 differ from the slow waves of 903-4 and 903-5. In particular, these later slow waves feature high frequency spike activity which is seen in the segments 903-41 and 903-51 respectively. As discussed above these segments indicate a peristaltic contraction in the gastrointestinal organ. Essentially, the present invention provides low energy pulse trains to regularize intrinsic slow wave activity along with higher energy pulse trains to elicit spike activity, i.e. to regularize motility disorders.

FIG. 7 depicts an alternate mode in which the device may operate. As seen, the output channel of the device delivers lower amplitude pulse trains 901-1 et seq. The sensing of a slow wave 903-1 causes the device of this embodiment to be triggered and emit a higher energy pulse train 902-1. Once the higher energy pulse train is delivered the device continues to deliver a series of lower energy pulse trains 901-4, -5 and -6. The sensing of slow wave 903-2 again causes the delivery of a higher energy pulse train 902-1. The lower energy and higher energy pulse trains delivered in this mode of the device are similar to that already detailed above.

Figure 8:
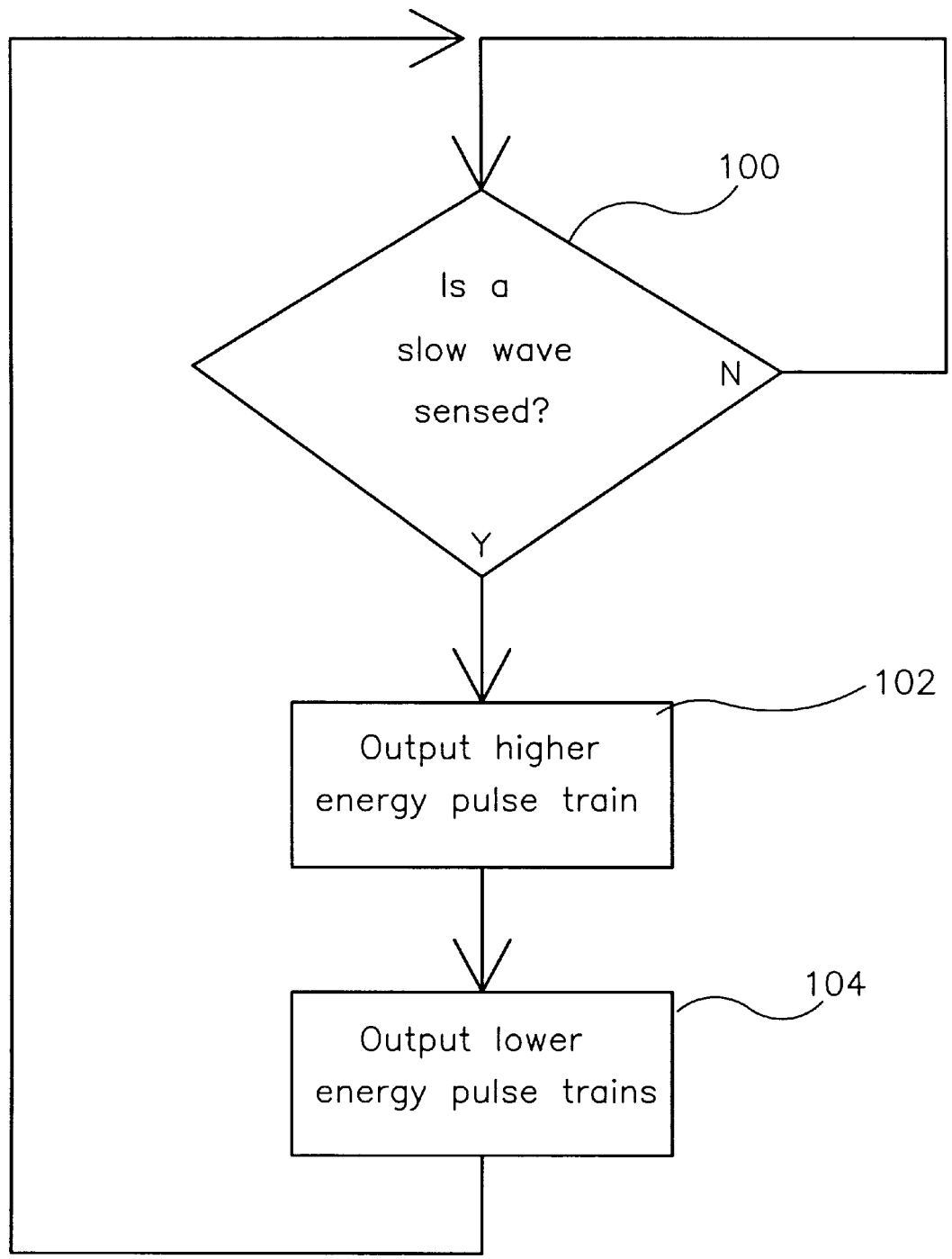
FIG. 8 is a flow chart showing the operation of the device illustrated in FIG. 7.

FIG. 8 is a flow chart showing the operation of the device illustrated in FIG. 7. As seen in step 100, the device determines whether a slow wave has been sensed. If no slow wave is sensed, the device continues in a sense mode whereby it continues to sense for any slow waves. Of course, the particular range of signals which would be sensed as a slow wave is programmable, and depends in part, upon the lead used as well as the location in which the lead is implanted within the gastrointestinal tract. If a slow wave is sensed, the device proceeds to block 102 in which it outputs a higher energy pulse train. As described above the output of this higher energy pulse train essentially is performed to elicit spike activity, i.e. to regularize motility within the stimulating portions of the gastrointestinal tract. Higher energy pulse trains may have an amplitude, frequency and duration as already described above. Next, the device turns to step 104 and outputs a lower energy pulse train or trains. As described above, these lower energy pulse trains are delivered to regularize intrinsic slow wave activity, thereby treating patient symptoms of nausea or vomiting, or both. A number of pulse trains, as well as any of their characteristics, e.g. amplitude, pulse duration, etc. may be set according to that already described above. Once the lower energy pulse train or trains have been set the device resets itself, returning again to step 100. In such a manner the device may operate to deliver electrical stimulation triggered by the sensing of slow wave activity.

Figure 9:
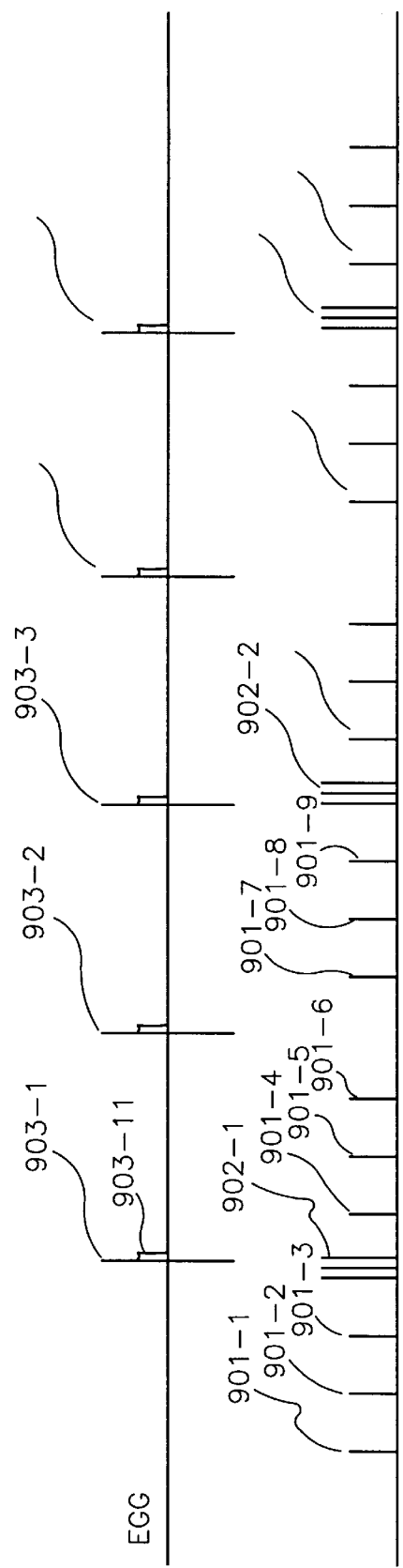
FIG. 9 depicts an alternate embodiment of the present invention which operates in an inhibited mode.

FIG. 9 depicts an alternate embodiment of the present invention which operates in an inhibited mode. As seen, the device continuously delivers the lower energy pulse train 901-1 et seq. The initiation of the delivery of lower energy pulse trains 901-1, -2 and -3 would open up the 902 timing window which upon expiring causes the delivery of higher energy pulse train 902-1. As seen, higher energy pulse train 902-1 evokes a slow wave 903-1 in the gastrointestinal organ. This slow wave, moreover, features a high frequency spike activity illustrated as component 903-11. As discussed above, this indicates peristaltic contraction is occurring. As seen, once the higher energy pulse train 902-1 is delivered the 901 timing window is begun which, upon expiration, causes the delivery of lower energy pulse trains 901-4, -5 and -6. When this delivery is begun another 902 timing window is again started, which, upon expiration, would cause the delivery of a higher energy pulse train. As seen, however, because the slow wave is sensed in the EGG this timing window is terminated, the delivery of a high energy pulse train is inhibited and, instead, a timing window is begun upon which the expiration of a low energy pulse train series will be scheduled 901-7, -8 and -9. The delivery of slow wave 901-7 again starts a timing window for the delivery of high energy pulse trains. As seen, when this timing window expires high energy pulse train 902-2 is delivered which thereby causes a corresponding slow wave 903-3 to be propagated within the EGG.

Figure 10:
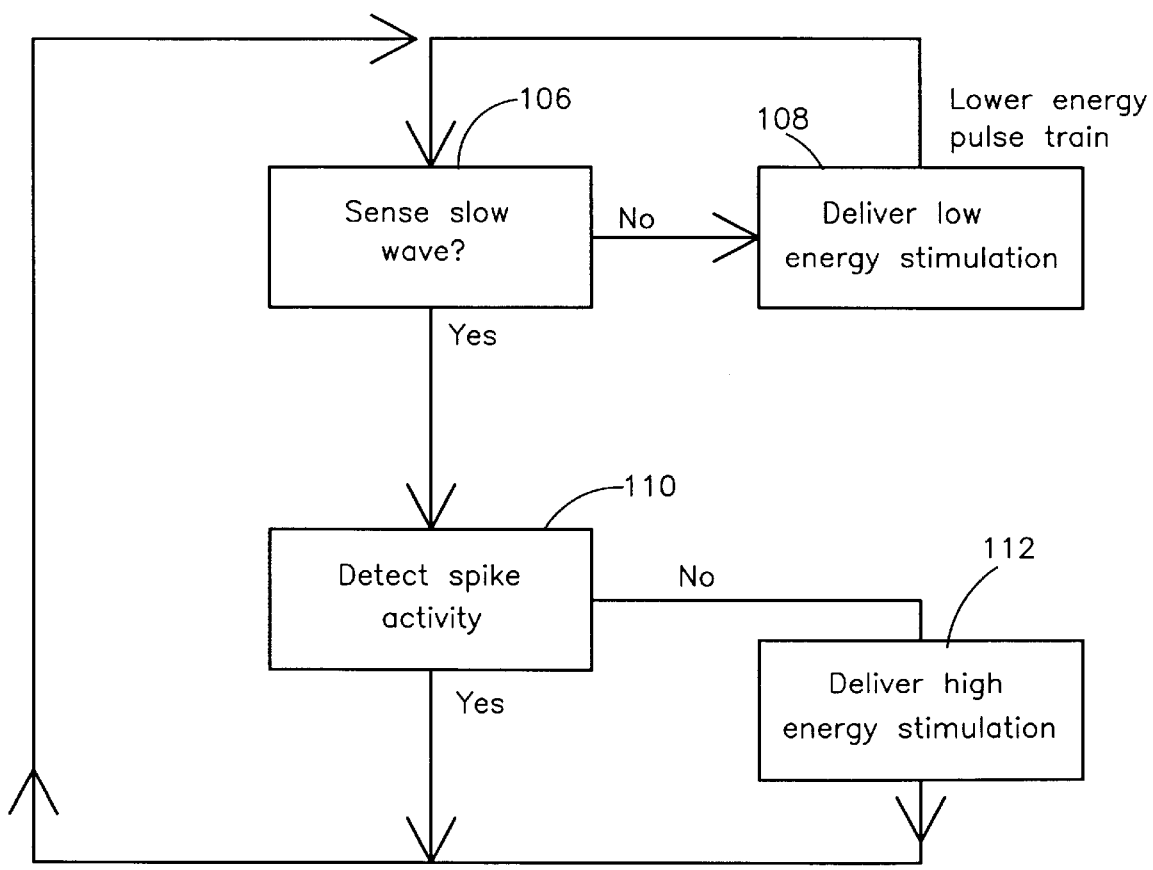
FIG. 10 is a flow chart illustrating the operation of the device depicted in FIG. 9.

FIG. 10 is a flow chart illustrating the operation of the device depicted in FIG. 9. As seen in block 106, the device senses whether slow wave activity is occurring. As described above, signals which would be characterised as slow wave activity may be programmed. If no slow wave activity is sensed the device proceeds to block 108 and delivers lower energy pulse train or trains. The particular stimulating portion used to stimulate the pulse train or trains is programmable and is within the parameters as described above. Once the lower energy pulse train is delivered in block 108 the device recycles again and returns to block 106. If slow waves are sensed in block 106, then the device proceeds to block 110. In block 110 the device determines whether any spike activity is sensed. As discussed above, spike activity comprises high frequency signals which are part of or immediately follow a slow wave. Of course, the exact type of signal which may be sensed as spike activity is programmable. If spike activity is sensed, then the device recycles and proceeds back to block 106 in which it determines whether slow waves are present. If no spike activity is detected in block 110, then the device proceeds to block 112 and delivers a lower energy pulse train or trains. As discussed above, these lower energy pulse train or trains are delivered to elicit spike activity, i.e. to regularize motility within the area of the gastrointestinal tract which is stimulated. Once such higher energy pulse train is delivered the device again recycles back to block 106. In such a manner the device may be seen to operate such that the detection of either a slow wave or spike activity within a slow wave causes the device to inhibit the lower energy pulse train or the higher energy pulse train respectively.

Figure 11:
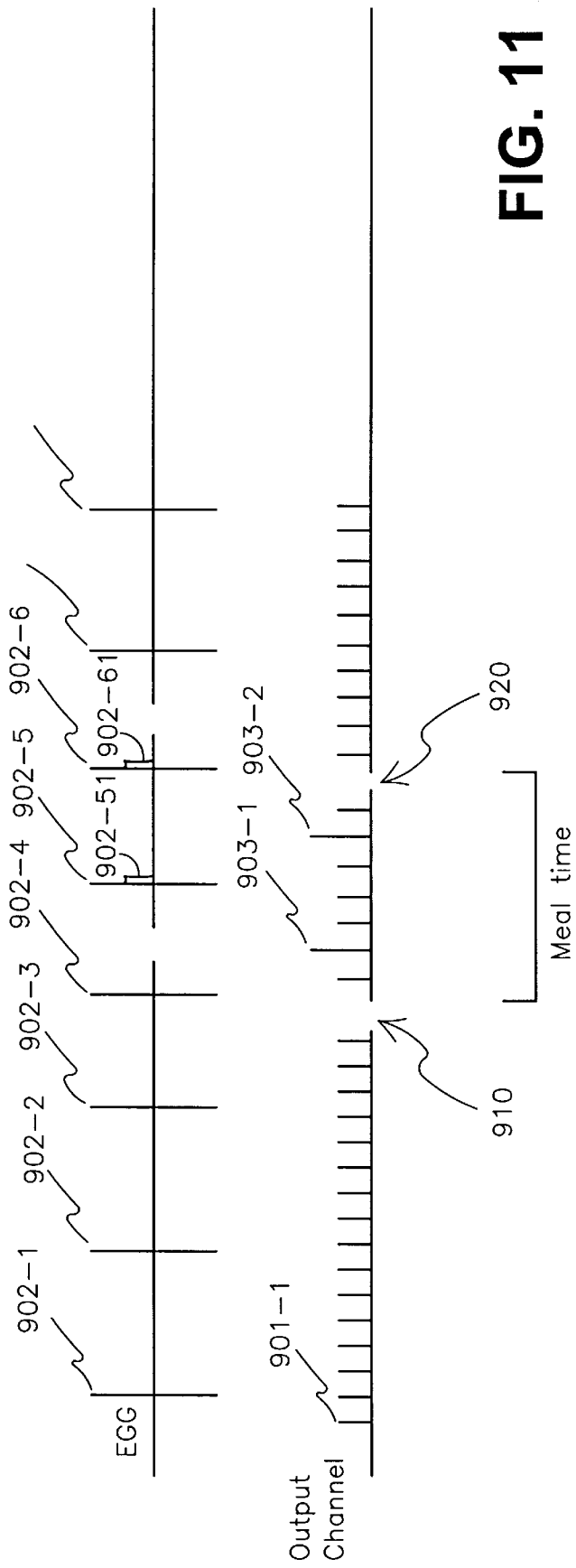
FIG. 11 depicts the operation of an alternate embodiment of the present invention.

FIG. 11 depicts the operation of an alternate embodiment of the present invention. In particular, in this embodiment the higher energy pulse trains are only delivered within a period corresponding to a meal time of the patient. As discussed below the sensing of meal time may be either performed by the device itself or may be patient activated. As seen, the device continues to emit low energy pulse trains 901-1 et seq. These pulse trains are delivered while slow wave activity occurs along the EGG 902-1, -2, -3 and -4. Upon the initiation of a meal time 910 the operation of the device changes and, the sensed EGG changes. In particular, during a meal a slow wave includes a high frequency spike activity component. This component indicates that peristaltic contractions of the organ are occurring. As discussed above, when there are no contents within the stomach slow waves occur but these do not cause peristaltic contractions to likewise occur which is before, during or after a meal (referred to generally, herein, as meal time). The slow wave morphology changes to include high frequency spike activity when peristaltic contraction occur. Thus, during meal time, healthy individuals typically have high frequency spike activity within their slow waves. In healthy individuals this indicates peristaltic contractions are occurring. As discussed above, in some patients, the high frequency spike activity occurs even though peristaltic contractions do not. In the present invention this high frequency spike activity may be sensed to cause the delivery of high energy pulses 903-1 and 903-2. As seen, each of these pulse trains evokes a corresponding slow wave 902-5 and 902-6 respectively having high frequency spike activity 902-51 and 902-61 respectively. Upon the end of meal time designated as 920 the delivery of high energy pulse trains is inhibited and only a series of low energy pulse trains is delivered. Thus as seen, in this embodiment, high energy pulse trains are only delivered to cause a contractile activity during a meal time. Moreover, at all other times low energy pulse trains are delivered.

Figure 12:
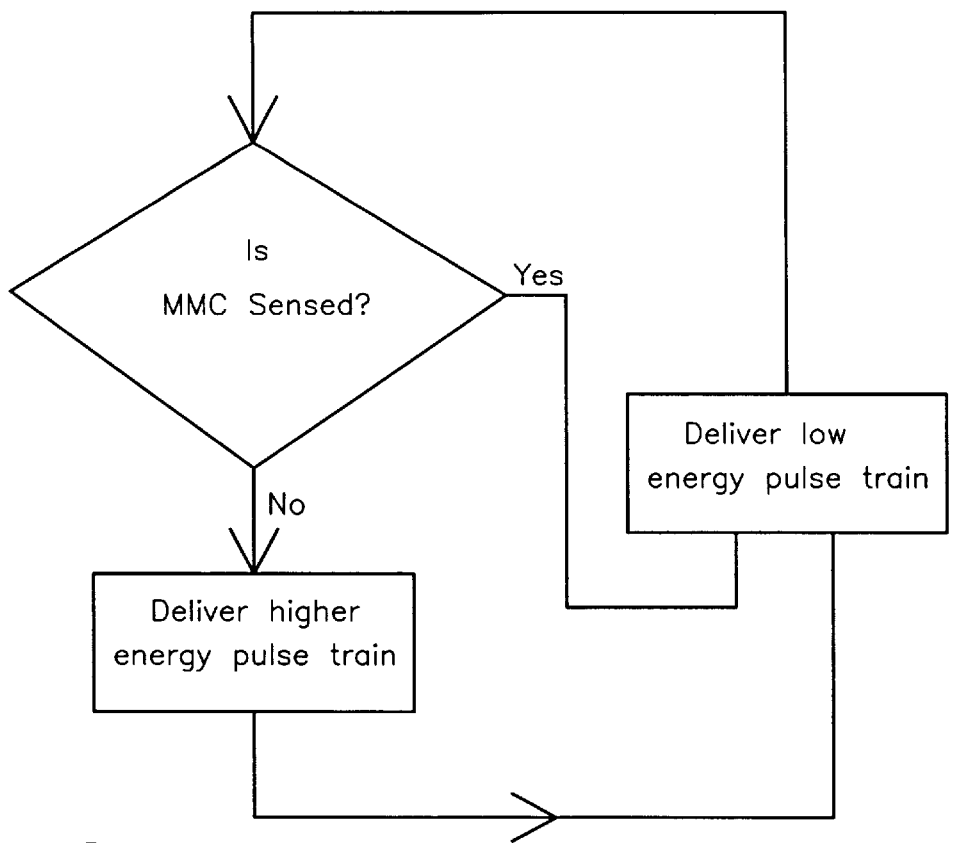
FIG. 12, 13, and 14 depict flow charts of the various manners in which the device illustrated in FIG. 11 may operate.
Figure 13:
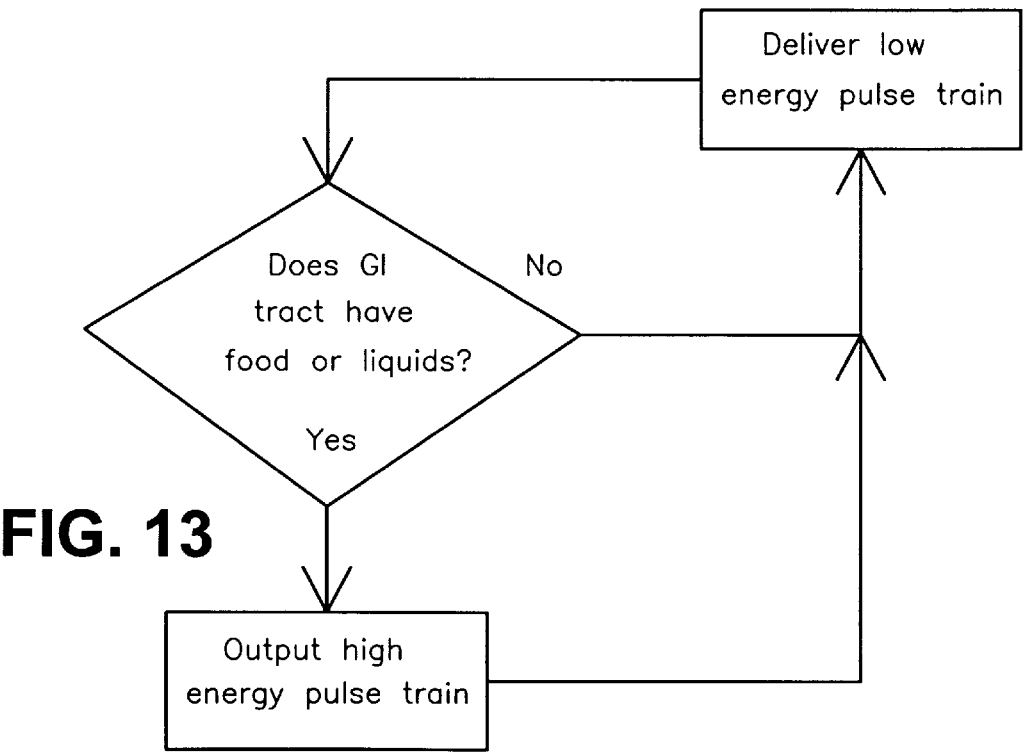
Figure 14:
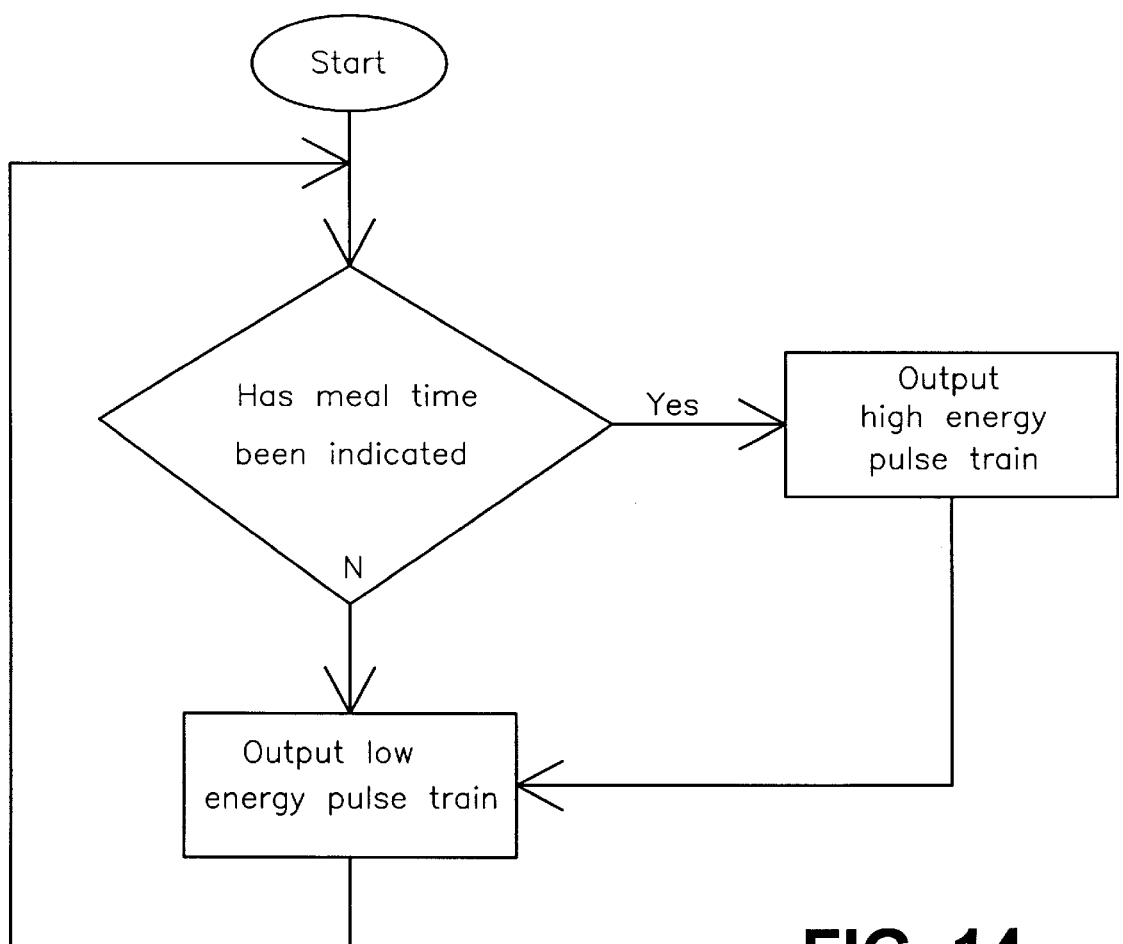

FIGS. 11, 12 and 13 depict flow charts of the various manners in which the device illustrated in FIG. 11 may operate. FIG. 11 discloses the operation of a device which senses the migrating motor complex before a higher energy pulse train is delivered. FIG. 12 depicts the operation of a device which senses the presence of food or liquid in the stomach before high energy pulse trains are delivered. Finally, FIG. 13 depicts the operation of a device which is patient controlled, i.e. the patient indicates to the device when meal time begins.

As discussed above, the device provides both lower energy and higher energy pulse train therapy to either, alone or simultaneously, treat the absence or irregular slow wave activity as well as the absence of corresponding spike activity. For the patient the device thus provides treatment to both vomiting and nausea as well as motility disorders within the area of the gastrointestinal tract to be stimulated. The device may be operated using either patient activation scheme such as a magnet-reed switch, ultrasound or infra red links, mechanical activation such as tapping on the device, or a hand patient programmer. As already discussed above, the device may further be activated through a timer by detection of contents within the stomach using mechanics. Moreover, although a single set of electrodes is shown as being used for sensing and stimulating the system, the present invention may simple use two sets of electrodes, one for stimulating and one for sensing. Moreover, the system could still further feature a third set of electrodes, one being used for sensing, the second set being used for the delivery of lower energy pulse trains while the third set could be used for the delivery of higher energy pulse trains.

Thus, as seen, the present invention provides a method and apparatus for treating two disorders of the gastrointestinal tract. Namely, the disorders treated are nausea and vomiting as well as motility disorders. The device provides this treatment by both sensing the underlying activity in the gastrointestinal tract as well as stimulating any response to this sensed activity. The device senses for both slow waves as well as spike activity. In response to the sensed signals, the device either delivers low energy pulse trains or high energy pulse trains, or both. A summary of the therapy matrix delivered by the present invention is shown below.

| Sense | | Stimulation | |
|---|---|---|---|
| Slow Wave | Spike Activity | Low Energy Pulse Train | High Energy Pulse Train |
| Present | Present | Inhibit | Inhibit |
| Absent | Absent | Stimulate | Stimulate |
| Present | Absent | Inhibit | Stimulate |
| Absent | Present | Stimulate | Inhibit |

While the present invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. An implantable system for providing electrical stimulation to the gastrointestinal tract comprising:
    fully implantable means for electrically coupling to the gastrointestinal tract; and
    an hermetically sealed implantable pulse generator coupled to the means for electrically coupling to the gastrointestinal tract, the pulse generator emitting a first type of electrical stimulation at a first rate and a second type of electrical stimulation at a second rate.

2. The system according to claim 1 wherein the first type of electrical stimulation is a first type of pulse train and wherein the second type of electrical stimulation is a second type of pulse train.

3. The system according to claim 2 wherein the first type of pulse train is an asynchronous stimulation train.

4. The system according to claim 3 wherein the asynchronous stimulation pulse trains have at least two pulses, the two pulses having an interpulse interval of between approximately 6–600 ms, an amplitude of between approximately 1–50 milliamps and pulsewidths between approximately 3–1000 microseconds.

5. The system apparatus according to claim 2 wherein the first pulse train has a first section and a second section, the first section having a first section frequency, the second section having a second section frequency.

6. The system according to claim 5 wherein the first section frequency is greater than the second section frequency.

7. The system according to claim 6 wherein the first pulse train has a first amplitude, and the second pulse train has a second amplitude.

8. The system according to claim 6 wherein the first amplitude is less than the second amplitude.

9. An apparatus for providing electrical stimulation to the gastrointestinal tract comprising:
    means for electrically coupling to the gastrointestinal tract;
    a sensor for sensing intrinsic gastrointestinal electrical activity between approximately 100 and 300 Hz, the sensor coupled to the means for electrically coupling to the gastrointestinal tract, the sensor emitting an intrinsic gastrointestinal electrical activity signal upon the sensing of intrinsic gastrointestinal electrical activity between approximately 100 and 300 Hz;
    a pulse generator coupled to the means for electrically coupling to the gastrointestinal tract and the sensor, the pulse generator emitting a first type of stimulation pulse trains at a first rate, the pulse generator emitting a second type of stimulation pulse trains at a second rate in response to the intrinsic gastrointestinal electrical activity signal.

10. The apparatus according to claim 9 further comprising means for switching the pulse generator from emitting a first type of stimulation pulse trains at a first rate to emitting a second type of stimulation pulse trains at a second rate, the switching means coupled to the pulse generator and further coupled to the sensor.

11. An apparatus for providing electrical stimulation to the gastrointestinal tract comprising:
    means for electrically coupling to a first area of the gastrointestinal tract;
    a sensor for sensing the presence of food or liquids within the first area of the gastrointestinal tract, the sensor emitting a mealtime signal upon the sensing of the presence of food or liquids within the first area of tie gastrointestinal tract; and
    a pulse generator coupled to the means for electrically coupling to the gastrointestinal tract and the sensor, the pulse generator emitting a first type of stimulation pulse train at a first rate, the pulse generator emitting a second type of stimulation pulse train at a second rate in response to the mealtime signal.

12. The apparatus according to claim 11 wherein the first type of pulse train is a high energy pulse train.

13. The apparatus according to claim 12 wherein the high energy pulse train comprises a series of at least one pulse.

14. The apparatus according to claim 13 wherein the at least one pulse has an amplitude between approximately 1 and 7 Volts.

15. The apparatus according to claim 13 wherein the high energy pulse train comprises a series of at least two pulses.

16. The apparatus according to claim 15 wherein the at least two pulses have amplitudes between approximately 1–50 milliamps and pulsewidths between approximately 3–1000 microseconds.

17. The apparatus according to claim 11 wherein the second type is a low energy pulse train delivered at a rate of between approximately 7–27 bpm.

18. The apparatus according to claim 17 wherein the low energy pulse train comprises a series of at least two pulses.

19. The apparatus according to claim 18 wherein the two pulses of the low energy pulse train have an interpulse interval between approximately 6–600 ms.

20. The apparatus according to claim 18 wherein the two pulses of the low encryp pulse train have amplitudes between approximately 1–50 milliamps.

21. The apparatus according to claim 18 wherein the two pulses of the low energy pulse train have pulsewidths between approximately 3–1000 microseconds.

22. An apparatus for providing electrical stimulation to the gastrointestinal tract comprising:

means for sensing slow waves;

means for sensing spike activity in a predefined period following the sensing of slow waves;

means for delivering a first type of pulse train stimulation;

means for inhibiting the means for delivering a first type of pulse train stimulation when a slow wave is sensed by the means for sensing slow waves;

means for delivery a second type of pulse train stimulation;

means for inhibiting the means for delivering a second type of pulse train stimulation when spike activity is sensed by the means for sensing spike activity.

23. The apparatus according to claim 22 wherein the first type of pulse train is a high energy pulse train.

24. The apparatus according to claim 23 wherein the high energy pulse train comprises a series of at least one pulse.

25. The apparatus according to claim 24 wherein the at least one pulse has an amplitude between approximately 1 and 7 Volts.

26. The apparatus according to claim 24 wherein the high energy pulse train comprises a series of at least two pulses.

27. The apparatus according to claim 26 wherein the at least two pulses have amplitudes of between approximately 1–50 milliamps and pulsewidths between approximately 3–1000 microseconds.

28. The apparatus according to claim 22 wherein the second type is a low energy pulse train delivered at a rate of between approximately 7–27 bpm.

29. The apparatus according to claim 28 wherein the low energy pulse train comprises a series of at least two pulses.

30. The apparatus according to claim 29 wherein the two pulses of the low energy pulse train have an interpulse interval between approximately 6–600 ms.

31. The apparatus according to claim 29 wherein the two pulses of the low energy pulse train have amplitudes between approximately 1–50 milliamps.

32. The apparatus according to claim 29 wherein the two pulses of the low energy pulse train have pulsewidths between approximately 3–1000 microseconds.

* * * * *

UNITED STATES PATENT AND TRADEMARK OFFICE
CERTIFICATE OF CORRECTION

PATENT NO.   : 6,091,992
DATED        : July 18, 2000
INVENTOR(S)  : Bourgeois et al.

It is certified that error appears in the above-identified patent and that said Letters Patent is hereby corrected as shown below:

Column 13,
Line 10, change "of the low encryp pulse" to -- of the low energy pulse --.

Signed and Sealed this

Eighteenth Day of March, 2003

JAMES E. ROGAN
*Director of the United States Patent and Trademark Office*